(12) United States Patent
Woo et al.

(10) Patent No.: US 11,160,495 B2
(45) Date of Patent: Nov. 2, 2021

(54) SLEEP APNEA MONITORING SYSTEM

(71) Applicant: BiLab Co., Ltd., Seoul (KR)

(72) Inventors: Eung Je Woo, Seongnam-si (KR); Tong In Oh, Suwon-si (KR)

(73) Assignee: BiLab Co., Ltd., Seoul (KR)

( * ) Notice: Subject to any disclaimer, the term of this patent is extended or adjusted under 35 U.S.C. 154(b) by 79 days.

(21) Appl. No.: 16/085,344

(22) PCT Filed: Mar. 7, 2017

(86) PCT No.: PCT/KR2017/002446
§ 371 (c)(1),
(2) Date: Sep. 14, 2018

(87) PCT Pub. No.: WO2017/160015
PCT Pub. Date: Sep. 21, 2017

(65) Prior Publication Data
US 2019/0076085 A1    Mar. 14, 2019

(30) Foreign Application Priority Data

Mar. 17, 2016  (KR) .................. 10-2016-0032398

(51) Int. Cl.
*A61B 5/00* (2006.01)
*A61B 5/053* (2021.01)
(Continued)

(52) U.S. Cl.
CPC .......... *A61B 5/4818* (2013.01); *A61B 5/0245* (2013.01); *A61B 5/0536* (2013.01);
(Continued)

(58) Field of Classification Search
CPC ........................ A61B 5/4818; A61B 5/0536
See application file for complete search history.

(56) References Cited

U.S. PATENT DOCUMENTS 9,615,773 B1\*  4/2017  Kayyali ................. A61B 5/103
2004/0186523 A1\*  9/2004  Florio ................ A61N 1/36514
                                                                  607/17
(Continued)

FOREIGN PATENT DOCUMENTS

KR  10-2006-0087852 A       8/2006
KR      20060087852 A   *   8/2006
(Continued)

OTHER PUBLICATIONS

International Search Report for PCT/KR2017/002446 dated May 23, 2017 (PCT/ISA/210).

*Primary Examiner* — Gary Jackson
*Assistant Examiner* — Zahed Kabir
(74) *Attorney, Agent, or Firm* — Sughrue Mion, PLLC

(57) ABSTRACT

The present invention relates to a sleep apnea monitoring system for monitoring the sleeping state of a user by means of impedance tomographic image information about the properties of biological tissue and biological signals of the user's body parts to be monitored. The present invention can be manufactured into a very simple portable device and thus enables monitoring during natural sleep at home. Therefore, the present invention enables utilization of obtained information during a sleeping state for diagnosis of and therapeutic plans for sleep apnea.

11 Claims, 4 Drawing Sheets

(51) Int. Cl.
    *A61B 5/0245*     (2006.01)
    *A61B 5/0402*     (2006.01)
    *A61B 5/085*     (2006.01)
    *A61B 5/08*     (2006.01)
    *A61B 5/1455*     (2006.01)
    *A61B 5/0536*     (2021.01)
    *A61B 5/318*     (2021.01)

(52) U.S. Cl.
    CPC ................ *A61B 5/08* (2013.01); *A61B 5/085* (2013.01); *A61B 5/0826* (2013.01); *A61B 5/1455* (2013.01); *A61B 5/318* (2021.01); *A61B 5/4809* (2013.01)

(56) References Cited

U.S. PATENT DOCUMENTS

| | | | | |
|---|---|---|---|---|
| 2008/0009755 A1* | 1/2008 | Patangay | ................ | A61B 7/00 600/484 |
| 2012/0016255 A1* | 1/2012 | Masuo | ................ | A61B 5/0809 600/547 |
| 2015/0224307 A1* | 8/2015 | Bolea | ................ | A61N 1/36196 607/42 |
| 2017/0079544 A1* | 3/2017 | Kim | ................ | A61B 5/004 |

FOREIGN PATENT DOCUMENTS

| | | |
|---|---|---|
| KR | 10-2013-0141289 A | 12/2013 |
| KR | 10-2015-0123186 A | 11/2015 |

\* cited by examiner

SLEEP APNEA MONITORING SYSTEM

CROSS REFERENCE TO RELATED APPLICATIONS

This application is a National Stage of International Application No. PCT/KR2017/002446 filed Mar. 7, 2017, claiming priority based on Korean Patent Application No. 10-2016-0032398 filed Mar. 17, 2016.

TECHNICAL FIELD

Example embodiments relate to a sleep apnea monitoring system, and more particularly, to a sleep apnea monitoring system that may monitor a sleeping state of a user based on impedance tomographic image information about properties of biological tissue and biological signals of a measurement target part of the user.

RELATED ART

Sleep apnea is a serious health and medical issue that may causes a heart disease, obesity, and accidents by fatigue and sleepiness, and the number of people suffering from sleep apnea is growing over the world.

Polysomnography (PSG) is primarily used for diagnosis of sleep apnea, and a sleep center runs a separate laboratory where a number of biosignal measuring devices including an electroencephalogram (EEG) measuring device and an image monitoring device are installed to perform PSG.

Sleep apnea includes obstructive sleep apnea and central sleep apnea.

Obstructive sleep apnea refers to a sleep breathing disorder that repeatedly causes frequent arousal and a decrease in blood oxygen saturation due to an occlusion in the upper airway during sleep, and is defined as a case in which an adult shows a decrease in a respiratory amplitude at least 90% from a baseline respiratory amplitude for a period of more than 10 seconds and respiratory efforts are maintained or increased at the same time.

Also, central sleep apnea is apnea caused by brain or heart problems and is defined as a case in which apnea occurs for more than 10 seconds and there is no respiratory effort.

For PSG that diagnoses such sleep apnea, a patient is requested to take sleep in a special-purpose laboratory while attaching various types of sensors to a body of the patient, and a PGS system analyzes various biosignals and image data measured during sleep and provides a doctor with information necessary for the diagnosis of sleep apnea.

Here, PSG refers to a test that provides objective data necessary for sleep disorder diagnosis and sleeping state evaluation by simultaneously recording (synchronizing) various physiological signals observed from a body during sleep, the signals such as an electroencephalogram (EEG), an electrooculogram (eye movement), a chin electromyogram (EMG), an electrocardiogram (ECG), a leg EMG, snoring, thoracic-abdominal respiration, a blood oxygen saturation, a respiratory airflow, and a position of the body during sleep.

However, a sleep testing method of performing the existing PSG is inappropriate to obtain data of a number of patients and make a diagnosis, is likely to provide a different result from that can be obtained during a natural sleeping state due to external and psychological factors and a space different from an ordinary sleeping site, and has difficulties in analyzing an effect of an actual level of apnea and an internal residual air volume on health.

Also, as the clinical importance of snoring and obstructive sleep apnea has been emerged in recent years, there is a growing demand for standard PSG. However, the test is complex, a lot of manpower and facilities are needed, a small number of clinics have test equipment, which makes a waiting time for reservation longer, and a financial burden of cost therefor is high. Thus, a necessity for a portable home sleep testing device that may substitute for the test has been increasing gradually.

With the increasing demand, innovative technology for measuring biosignals has been developed, and many studies on the effectiveness and validity of portable home sleep testing devices using such technology have been conducted. The American Academy of Sleep Medicine (AASM) suggested six categories in 2010.

The AASM announced that clinicians may diagnose and treat sleep apnea through a combination of various biosignals measured within the categories. Here, the six categories include sleep, cardiovascular, oximetry, position, effort and respiratory.

The following [Table 1] shows a categorization system according to the six categories.

TABLE 1

| Sleep | Cardiovascular | Oximetry | Position | Effort | Respiratory |
| --- | --- | --- | --- | --- | --- |
| $S_1$ - Sleep by 3 EEG channels* with EOG and chin EMG | $C_1$ - more than 1 ECG lead - can derive events | $O_1$ - Oximetry (finger or ear) with recommended sampling | $P_1$ - Video or visual position measurement | $E_1$ - 2 RIP belts | $R_1$ - Nasal pressure and thermal device |
| $S_2$ - Sleep by less than 3 EEG* with or without EOG or chin EMG | $C_2$ - Peripheral arterial tonometry | $O_{1a}$ - Oximetry (finger or ear) without recommended sampling (per Scoring Manual) or not described | $P_2$ - Non-visual position measurement | $E_2$ - 1 RIP belt | $R_2$ - Nasal pressure |
| $S_3$ - Sleep surrogate; e.g. actigraphy | $C_3$ - Standard ECG measure (1 lead) | $O_2$ - Oximetry with alternative site (e.g. forehead) | | $E_3$ - Derived effort (e.g. forehead versus pressure, FVP) | $R_3$ - Thermal device |

TABLE 1-continued

| Sleep | Cardiovascular | Oximetry | Position | Effort | Respiratory |
|---|---|---|---|---|---|
| S$_4$ - Other sleep measure | C$_4$ - Derived pulse (typically from oximetry) | O$_3$ - Other oximetry | | E$_4$ - Other effort measure (including piezo belts) | R$_4$ - End-Tidal CO$_2$ (ETCO$_2$) |
| | C$_5$ - Other cardiac measure | | | | R$_5$ - Other respiratory measure |

Here, sleep includes an electroencephalography and a body movement measurement during sleep, cardiovascular includes an electrocardiography, a peripheral arterial tonometry (PAT) and a heart rate, and oximetry includes a 3-second averaging measurement function and a minimum of 10-hertz (Hz) sampling rate.

Also, effort includes an ability of respiratory effort when apnea occurs, and respiratory includes a sensor to determine apnea, hypopnea, and normal respiration.

The following [Table 2] shows product groups developed and released by selectively combining the six categories according to technology of each company.

TABLE 2

| Device Name | Sleep | Cardiac | Oximetry | Position | Effort | Respiratory |
|---|---|---|---|---|---|---|
| Apoeat.ink (Ng 2009) | 0 | 4 | 1x | 0 | 0 | 2 |
| Apnoescreen I (Golpe 2002) | 3 | 4 | 1x | 2 | 0 | 3 |
| Apnoescreen II (Garcia-Diaz 2007) | 3 | 3 | 1x | 2 | 4 | 3 |
| ARES (Wedbrock 2005) | 3 | 4 | 2 | 2 | 0 | 5 |
| ARES (Ayappa 2008 To 2009) | 3 | 4 | 2 | 2 | 3 | 2 |
| Compusmedica PS-2 (Iber 2004) | 2 | 3 | 1x | 0 | 1 | 3 |
| Embletta PDS (Ng 2010) | 0 | 4 | 1x | 2 | 1 | 2 |
| Embletta (Dingli 2003) | 0 | 0 | 1x | 2 | 4 | 2 |
| Morpheux Hx software with standard hospital signals (Amir 2010) | 4 | 3 | 1x | 0 | 4 | 4 |
| Northeast Monitoring Hoiter-oximeter (Heneghan 2008) | 0 | 3 | 1x | 0 | 0 | 0 |
| Novasom QSG/Bedbugg/Silent Night (Richert 2003) | 0 | 4 | 1x | 0 | x | 5 |
| Novasom QSG/Bedbugg/Silent Night (Claman 2001) | 0 | 4 | 1x | 0 | 4 | 5 |
| Rammers/SnoreSat (Jobin 2007) | 0 | 0 | 1x | 2 | 0 | 5 |
| Siesta (Campbell 2010) | 2 | 3 | 1x | 2 | 4 | 1 |
| SNAP (Michaelson 2006) | 0 | 4 | 1x | 0 | 0 | 5 |
| SNAP (Su 2004) | 0 | 4 | 1x | 0 | x | 5 |
| Somté/Morpheus (Takama 2010) | 0 | 4 | 1x | 0 | x | 3 |
| Stardual il (Yin 2006, Sanbos-Silva 2009) | 0 | 4 | 1x | 2 | 4 | 2 |
| WatchPAT (Bar 2003) | 0 | 2 | 1x | 2 | 0 | 0 |
| WatchPAT (Ayas 2003, Pittman 2004, Pittman 2006, Zou 2006, Pang 2007, Choi 2010) | 3 | 2 | 1x | 2 | 0 | 0 |

Referring to [Table 2], WatchPAT provides two items of heart-related information (a PAT signal and a heart rate provided by an oxygen saturation measuring module), an oxygen saturation, position information, and data to diagnose a sleeping state by calculating such information using a predetermined algorithm.

However, WatchPAT is an indirect method of diagnosing sleep apnea, of which an accuracy has not been verified and which is difficult to apply to hypertension patients and incapable of distinguishing between obstructive sleep apnea and central sleep apnea.

Thus, the present disclosure describes a new biometric information-based sleep apnea monitoring system that may solve the problems of professional or portable sleep apnea diagnosis devices including WatchPAT and PSG.

DISCLOSURE OF THE INVENTION

Technical Goals

An aspect provides a sleep apnea monitoring system that may monitor obstructive sleep apnea in real time based on impedance tomographic image information, the obstructive sleep apnea occurring in response to an airway being obstructed by movements of muscles in an upper airway.

Also, an aspect provides a sleep apnea monitoring system that may clearly distinguish between obstructive sleep apnea and central sleep apnea in which a change in air distribution in lungs decreases sharply, by measuring and detecting the change in air distribution in the lungs from impedance tomographic image information.

Also, an aspect provides a sleep apnea monitoring system that may monitor an effect of upper airway obstruction on a human body in real time through an amount of residual air and a change therein, thereby acquiring an incredibly immediate result when compared to information measured from a change in blood oxygen saturation which is secondary indirect information occurring by sleep apnea.

Also, an aspect provides a sleep apnea monitoring system that may be manufactured into a very simple portable device capable of simultaneously measuring both impedance tomographic image information and biosignals or a selected portion thereof, thereby enabling measurement during natural sleep at home and being used for diagnosis and treatment planning of sleep apnea by utilizing sleeping state information obtained therethrough.

Solutions

According to an aspect of an example embodiment, there is provided a sleep apnea monitoring system including an electrical impedance tomography (EIT) electrode unit including a plurality of EIT electrodes to be attached to a surface of a measurement target part of a user to measure impedance data of the measurement target part, a sensing unit to be in contact with the measurement target part of the user to sense a biosignal, and a sleep monitoring device configured to output impedance tomographic image information about properties of biological tissue of the measurement target part based on the measured impedance data and monitor a sleeping state of the user based on the output impedance tomographic image information and the sensed biosignal.

The sleep monitoring device may include an image outputter configured to output the impedance tomographic image information by imaging the properties of the biological tissue of the measurement target part based on the measured impedance data; a biosignal analyzer configured to analyze the biosignal including at least one of a blood oxygen saturation, a sound, a position, and an electrocardiogram (ECG) of the measurement target part of the user sensed by the sensing unit; a sleeping state detector configured to detect the sleeping state of the user based on the output impedance tomographic image information and the analyzed biosignal; and a controller configured to control diagnosis information with respect to the detected sleeping state to be provided to the user.

The image outputter may include a current injecting module configured to inject currents having a plurality of frequency ranges through at least one EIT electrode pair selected from the plurality of EIT electrodes attached to the measurement target part; and a voltage measuring module configured to measure a voltage induced in response to the injected currents through an EIT electrode pair unselected from the plurality of EIT electrodes.

Also, the image outputter may further include an impedance measuring module configured to measure the impedance data based on the voltage measured through the voltage measuring module, the voltage that changes depending on the sleeping state of the user; and an impedance tomographic image information generating module configured to generate the impedance tomographic image information by imaging the properties of the biological tissue based on the measured impedance data.

The plurality of EIT electrodes may be arranged on one surface of a base plate formed of a flexible material and attached to the surface of the measurement target part.

The sensing unit may include at least one of a blood oxygen saturation measuring sensor configured to measure a blood oxygen saturation signal in arterial blood of the measurement target part, a sound detecting sensor configured to detect a sound by a biological activity of the user, a position measuring sensor configured to sense a movement of the user, and an ECG measuring sensor configured to measure an ECG of the measurement target part, when the user is in the sleeping state.

Also, the sleeping state detector may be configured to detect a sleeping state of respiration or apnea of the user from ECG morphology by the output impedance tomographic image information and the analyzed biosignal.

Also, the sleeping state detector may be configured to detect a sleeping state of obstructive sleep apnea or central sleep apnea based on the output impedance tomographic image information and the analyzed biosignal, when the user is in the sleeping state of apnea.

Also, the sleeping state detector may be configured to detect a sleeping state of rapid eye movement (REM) sleep or non-REM sleep of the user based on the output impedance tomographic image information and the analyzed biosignal.

Also, the sleeping state detector may be configured to detect a sleeping state of sleep or wake of the user based on the output impedance tomographic image information and a heart rate analyzed from an ECG, when the ECG is measured as the biosignal.

The sleep monitoring device may further include a user interface (UI) configured to display at least one of the detected sleeping state, the diagnosis information with respect to the sleeping state, and the output impedance tomographic image information for the user; and a communicator configured to transmit the diagnosis information with respect to the sleeping state.

According to an aspect of an example embodiment, there is provided a sleep apnea monitoring system including an image outputter configured to output impedance tomographic image information by imaging properties of biological tissue of a measurement target part of a user based on impedance data of the measurement target part measured by a plurality of electrical impedance tomography (EIT) electrodes attached to a surface of the measurement target part; a biosignal analyzer configured to analyze a biosignal including at least one of a blood oxygen saturation, a sound, a position, and an electrocardiogram (ECG) of the measurement target part of the user sensed by a sensing unit being in contact with the measurement target part of the user; a sleeping state detector configured to detect a sleeping state of the user based on the output impedance tomographic image information and the analyzed biosignal; and a controller configured to control diagnosis information with respect to the detected sleeping state of the user to be provided to the user.

Effect

According to example embodiments, it is possible to monitor obstructive sleep apnea in real time based on impedance tomographic image information, the obstructive sleep apnea occurring in response to an airway being obstructed by movements of muscles in an upper airway.

Also, according to example embodiment, it is possible to clearly distinguish between obstructive sleep apnea and central sleep apnea in which a change in air distribution in lungs decreases sharply, by measuring and detecting the change in air distribution in the lungs from impedance tomographic image information.

Also, according to example embodiment, it is possible to monitor an effect of upper airway obstruction on a human body in real time through an amount of residual air and a change therein, thereby acquiring an incredibly immediate result when compared to information measured from a change in blood oxygen saturation which is secondary indirect information occurring by sleep apnea.

Also, according to example embodiment, it is possible to manufacture a sleep apnea monitoring system into a very simple portable device capable of simultaneously measuring both impedance tomographic image information and biosignals or a selected portion thereof, thereby enabling measurement during natural sleep at home and being used for diagnosis and treatment planning of sleep apnea by utilizing sleeping state information obtained therethrough.

BEST MODE

Figure 1:
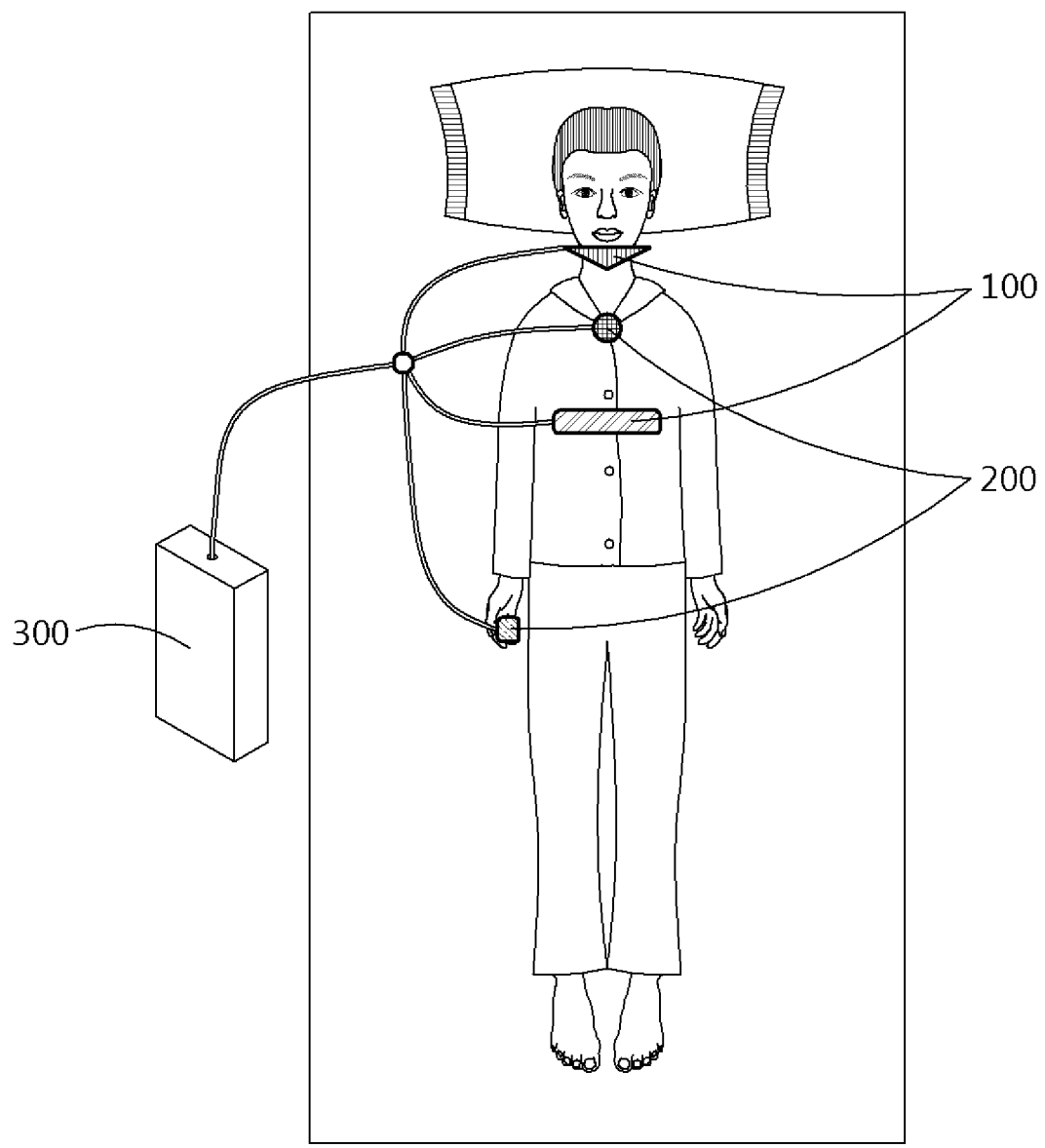
FIG. 1 illustrates an example of implementing a sleep apnea monitoring system according to an example embodiment.

Hereinafter, example embodiments will be described in detail with reference to the accompanying drawings and the content disclosed in the drawings. However, the present disclosure should not be construed as being limited to the example embodiments set forth herein.

The terminology used herein is for the purpose of describing particular example embodiments only and is not intended to limit the scope of disclosure in any way. As used herein, the singular forms "a", "an", and "the" are intended to include the plural forms as well, unless the context clearly indicates otherwise. It will be further understood that the terms "comprises/comprising" and/or "includes/including" when used herein, specify the presence of stated elements, steps, operations, and/or components, but do not preclude the presence or addition of one or more elements, steps, operations and/or components and/or groups thereof.

Also, "example embodiment", "example", "aspect", instance", etc., as used herein are not intended to indicate that the described aspect or design is better or more advantageous than other aspects or designs.

Also, the term "or" is intended to mean an inclusive "or" rather than an exclusive "or". That is, unless specified otherwise or clear from the context, the phrase "x employs a or b" is intended to mean any of natural inclusive permutations.

In addition, the articles "a" or "an" as used in this specification and the claims should generally be construed to mean "one or more" unless specified otherwise or clear from the context to be directed to a singular form.

Terms, such as first, second, and the like, as used in the specification and the claims may be used herein to describe components. The components are not limited thereto. Each of the terminologies is used merely to distinguish a corresponding component from other component(s).

Unless otherwise defined, all terms, including technical and scientific terms, used herein have the same meaning as commonly understood by one of ordinary skill in the art to which this disclosure pertains. Terms, such as those defined in commonly used dictionaries, are to be interpreted as having a meaning that is consistent with their meaning in the context of the relevant art, and are not to be interpreted in an idealized or overly formal sense unless expressly so defined herein.

In the meantime, when it is determined detailed description related to a related known function or configuration they may make the purpose of this disclosure unnecessarily ambiguous in describing the example embodiments, the detailed description will be omitted here. Also, terms used herein are defined to appropriately describe the example embodiments and thus may be changed depending on a user, the intent of an operator, or a custom. Accordingly, the terms must be defined based on the following overall description of this specification.

FIG. 1 illustrates an example of implementing a sleep apnea monitoring system according to an example embodiment.

The sleep apnea monitoring system may measure impedance data of a measurement target part of a user, sense a biosignal, output impedance tomographic image information about properties of biological tissue of the measurement target part based on the measured impedance data, and monitor a sleeping state of the user based on the output impedance tomographic image information and the sensed biosignal.

To achieve the foregoing, the sleep apnea monitoring system may include an electrical impedance tomography (EIT) electrode unit 100, a sensing unit 200, and a sleep monitoring device 300.

The EIT electrode unit 100 may include a plurality of EIT electrodes to be attached to a surface of the measurement target part of the user to measure the impedance data of the measurement target part.

The plurality of EIT electrodes may be arranged on one surface of a base plate formed of a flexible material and attached to the surface of the measurement target part.

Also, the plurality of EIT electrodes may be used to inject relatively low currents that the user may not sense, for example, high-frequency currents below 1 milliampere (mA), and measure an induced voltage, and the current-voltage data measured through the plurality of EIT electrodes may be used to detect a shape of an upper airway or a shape of a chest through an imaging algorithm.

According to an example embodiment, the EIT electrode unit 100 may be formed at a predetermined interval on the base plate or may be disposed in various arrangements and structures depending on a property of the measurement target part and a purpose of utilization. Also, the base plate may have a predetermined length and a predetermined area such that the base plate may be worn around the measurement target part including the upper airway and the chest or an abdomen of the user to measure the impedance. However, the length and the area may be changeable depending on an example embodiment and thus, are not limited thereto.

Also, according to an example embodiment, the EIT electrode unit 100 of the sleep apnea monitoring system may be formed on a belt- or mask-shaped protection gear configured to surround the outside of the plurality of EIT electrodes to protect the plurality of EIT electrodes attached to a facial skin in the vicinity of an upper airway region.

The protection gear of the above shape may simultaneously reduce a level of pressure that the user may feel during natural sleep and maintain a level of contact sufficient to measure an induced voltage, thereby greatly reducing the level of pressure when compared to that of an existing ultrasonic probe. Thus, whether the upper airway of the user is obstructed may be easily measured in a natural sleeping state for a relatively long time using the EIT electrode unit 100 of the above structure.

Also, the EIT electrode unit 100 may be attached to the upper airway or the chest of the user to effectively measure a distribution of electric field on a surface in the vicinity of the upper airway or the chest through a change of electrode arrangement structure and measurement protocol by arranging the plurality of EIT electrodes in a two-dimensional or three-dimensional structure.

The sensing unit 200 may be in contact with the measurement target part of the user and sense the biosignal.

The sensing unit 200 may include a fabric-based sensor and perform a function of sensing the biosignal of the user who is sleeping using the fabric-based sensor.

For example, the sensing unit 200 may include at least one of a blood oxygen saturation ($SpO_2$) measuring sensor configured to measure a blood oxygen saturation signal in arterial blood of the measurement target part, a sound detecting sensor configured to detect a sound by a biological activity of the user, a position measuring sensor configured to sense a movement of the user, and an electrocardiogram (ECG) measuring sensor configured to measure an ECG of the measurement target part, when the user is in the sleeping state.

Here, the blood oxygen saturation measuring sensor may be attached to the measurement target part of the user and measure the blood oxygen saturation ($SpO_2$, saturation of peripheral oxygen) that represents a content of oxygen in haemoglobin among a number of components constituting the blood.

According to an example embodiment, the blood oxygen saturation measuring sensor may measure a photoplethysmography (PPG) signal of a body of the user reflected or transmitted by using light and measure the blood oxygen saturation based on the measured PPG signal.

Also, the sound detecting sensor may sense a sound of at least one of breathing, snoring, crying and talking in sleep. According to an example embodiment, the sound detecting sensor may be attached to the measurement target part of the user or may be a contact-free sensor that exists separate a predetermined distance from the user.

Also, the position measuring sensor may be formed from at least one of a gyro sensor and an acceleration sensor and attached to the measurement target part of the user to measure the position based on a movement of the user.

For example, the position measuring sensor may detect a change in sleeping position of the user, for example, detect a change in the sleeping position in response to the user lying while sleeping or the user sitting or standing while being awake, using the acceleration sensor.

Also, the ECG measuring sensor may be in contact with the measurement target part of the user and measure the ECG.

Here, the ECG is a waveform that represents action potential occurring by a special excitatory & conductive system of a heart using a vector sum. That is, the ECG refers to a vector sum signal of active potential occurring at the constituents of the heart, for example, a sinoatrial node (SA node), an atrioventricular node (AV node), a His bundle, bundle branches, and Purkinje fibers, the signal measured by the electrodes attached to a covering of the body.

The sensing unit 200 of the sleep apnea monitoring system may further include, according to an example embodiment, a sleep environment sensor configured to measure a sleep environment, and the sleep environment sensor may be positioned at a predetermined distance from the user and measure at least one of noise, light, vibration and temperature in a sleeping space.

Hereinafter, the configurations of the EIT electrode unit 100 and the sensing unit 200 will be described further with reference to FIGS. 2A and 2B.

Figure 2A:
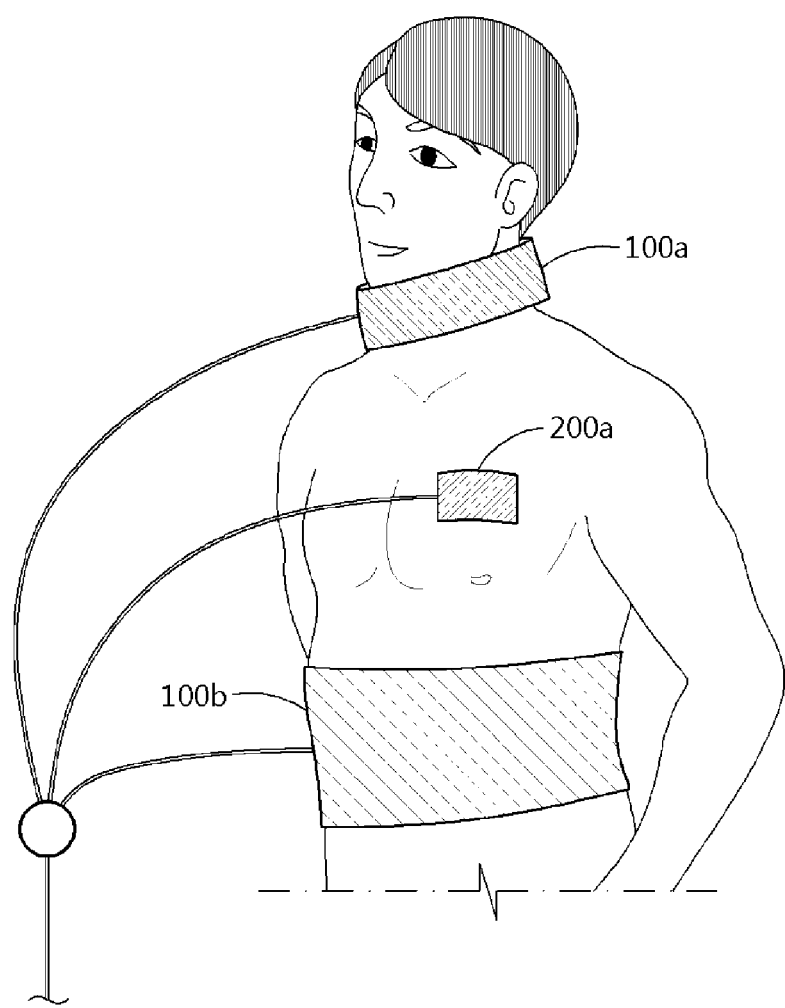
FIGS. 2A and 2B illustrate examples of electrical impedance tomography (EIT) electrode units and a sensing unit of a sleep apnea monitoring system according to an example embodiment.

FIG. 2A illustrates an example of EIT electrode units and a sensing unit of a sleep apnea monitoring system with respect to a measurement target part according to an example embodiment.

Referring to FIG. 2A, the sleep apnea monitoring system may include EIT electrode units 100a and 100b respectively attached to the upper airway and the chest of the user and a sensing unit 200a attached to the measurement target part of the user.

The EIT electrode unit 100a attached to the upper airway of the user may be formed on a base plate at a predetermined interval, be attached to a facial skin in the vicinity of an upper airway region, and measure impedance data related to opening and closing of the upper airway.

Here, the base plate on which the EIT electrode unit 100a may be formed as at least one of a mask-shaped plate, a belt-shaped plate, an electrode belt and a cable belt, but is not necessarily limited thereto. In addition, in view of a level of contact to increase a data measurement level while minimizing a pressure that the user may feel during natural sleep, a base plate including an EIT electrode unit 100a of an arrangement having a different shape or structure may also be sufficiently applied.

According to an example embodiment, the EIT electrode unit 100a may include a conductive fiber electrode manufactured using a silver (Ag)-plated elastic fiber or a polymer-based nanofiber (polyvinylidene fluoride (PVDF) nanofiber web), but, according to an example embodiment, may include electrodes of various materials which show less dermal response with respect to long-time measurement and thus, is not limited thereto.

Also, the EIT electrode unit 100a may effectively measure a distribution of electric field on a surface in the vicinity of the upper airway of the user through a change of electrode arrangement structure and measurement protocol by arranging electrodes of at least one of, for example, 16, 32, 64 and 256 channels in a two-dimensional or three-dimensional structure.

According to an example embodiment, the EIT electrode unit 100a formed on the base plate may be disposed in the three-dimensional arrangement so as to enable impedance measurement corresponding each layer, thereby promoting an accurate and effective diagnosis, when compared to an existing method that provides only a two-dimensional cross-sectional image at a predetermined location.

The EIT electrode unit 100b of the sleep apnea monitoring system attached to the chest of the user may be formed on the base plate having a predetermined length such that the base plate may be worn around the measurement target part of the user to measure the impedance. Also, the base plate may be formed of a flexible material such that the base plate may be worn on a curved part like a waist or a chest of a human body.

As shown in FIG. 2A, the EIT electrode unit 100b may be formed on the base plate while maintaining a predetermined distance and attached to the chest of the user to measure the impedance from a shape of lungs in response to respiration while the user is in a sleeping state.

According to an example embodiment, the base plate on which the EIT electrode unit 100b is formed is not necessarily limited to the shape of the belt-shaped array electrodes. In addition, in view of a level of contact to increase a data measurement level while minimizing a pressure that the user may feel during natural sleep, a base plate including an EIT electrode unit 100a of an arrangement having a different shape or structure may also be sufficiently applied.

The sensing unit 200a of the sleep apnea monitoring system attached to the measurement target part of the user may be in contact with the measurement target part of the user and sense a biosignal.

The sensing unit 200a may be in contact with any site of the measurement target part of the user, and thus a contact location of the measurement target part and a number thereof are not limited to the example of FIG. 2A.

The sensing unit 200a may be at least one of a sound detecting sensor, a position measuring sensor and an ECG measuring sensor, and may be a fiber-based sensor to be attached to a body of the user.

Figure 2B:
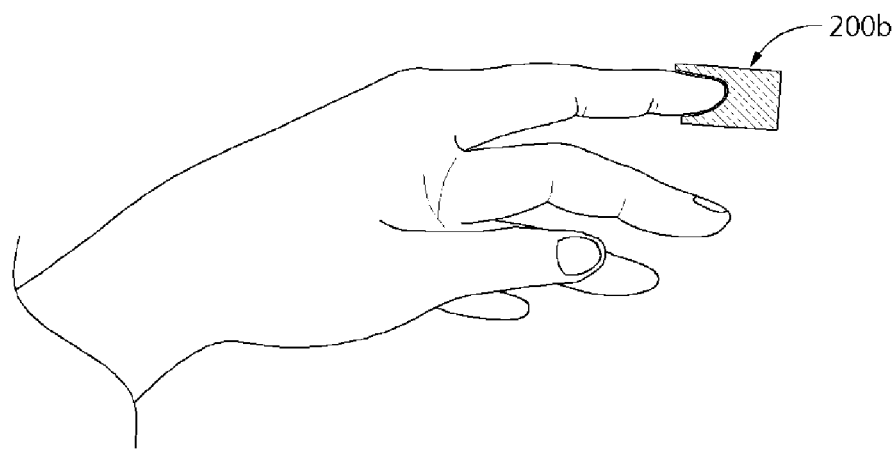

FIG. 2B illustrates an example of a sensing unit of a sleep apnea monitoring system for measuring a blood oxygen saturation according to an example embodiment.

Referring to FIG. 2B, to measure a blood oxygen saturation of a user, the sleep apnea monitoring system may include a sensing unit 200b configured to measure an oxygen saturation ($SpO_2$) signal using a red-light source in conjunction with an optical sensor that measures an amount of light transmitted through blood flowing in a peripheral blood vessel of a fingertip or a toe.

As shown in FIG. 2B, the sensing unit 200b may be provided in a form of a measurement terminal to be worn on a fingertip and include a red light emitting diode (LED) of 660 nanometers (nm) and an infrared LED of 940 nm in a light emitting unit and an optic module to which a photodiode and a phototransistor are attached in a light receiving unit.

Referring to FIG. 1 again, the sleep monitoring device 300 of the sleep apnea monitoring system may output impedance tomographic image information about properties of biological tissue of the measurement target part based on the measured impedance data and monitor a sleeping state of the user based on the output impedance tomographic image information and the sensed biosignal.

In further detail, the sleep monitoring device 300 may be connected to the EIT electrode unit 100 and the sensing unit 200, output the impedance tomographic image information about the properties of the biological tissue by receiving the impedance data of the measurement target part measured by the EIT electrode unit 100 and the biosignal measured by the sensing unit 200, and monitor the sleeping state of the user based on the impedance tomographic image information and the biosignal.

Hereinafter, the configuration of the sleep monitoring device 300 will be described further with reference to FIG. 3.

Figure 3:
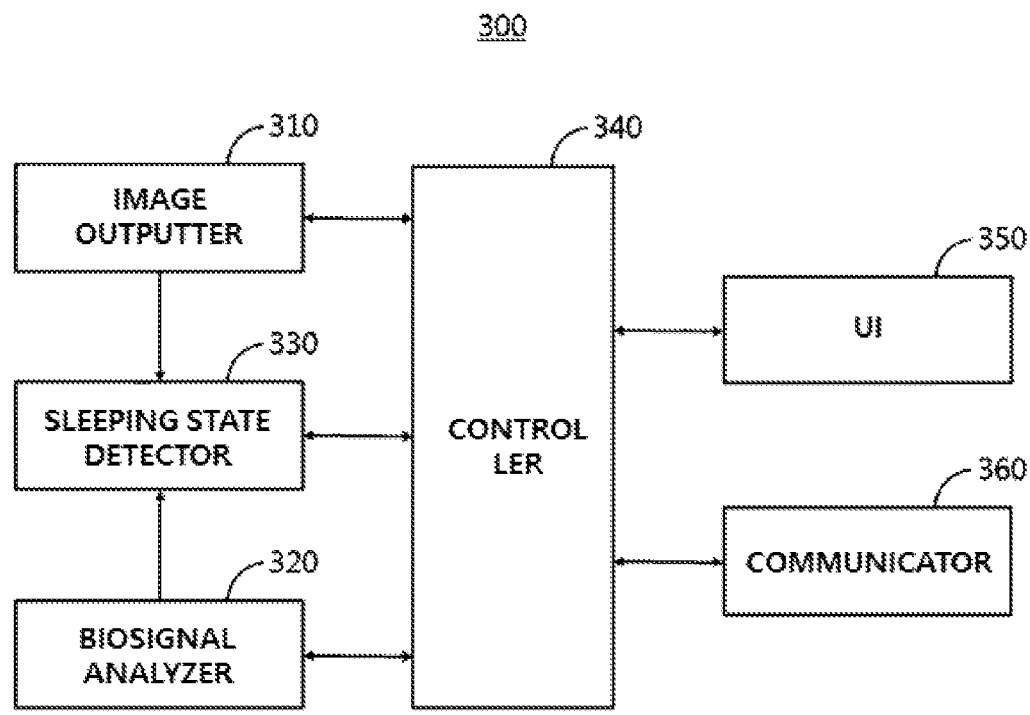
FIG. 3 is a block diagram illustrating a configuration of a sleep monitoring device of a sleep apnea monitoring system according to an example embodiment.

FIG. 3 is a block diagram illustrating a configuration of a sleep monitoring device of a sleep apnea monitoring system according to an example embodiment.

Referring to FIG. 3, the sleep monitoring device 300 may the output impedance tomographic image information based on the impedance data and monitor the sleeping state of the user based on the output impedance tomographic image information and the biosignal.

To achieve the foregoing, the sleep monitoring device 300 may include an image outputter 310, a biosignal analyzer 320, a sleeping state detector 330 and a controller 340.

The image outputter 310 may output the impedance tomographic image information by imaging the properties of the biological tissue of the measurement target part based on the measured impedance data.

Hereinafter, the configuration of the image outputter 310 will be described further with reference to FIG. 4.

Figure 4:
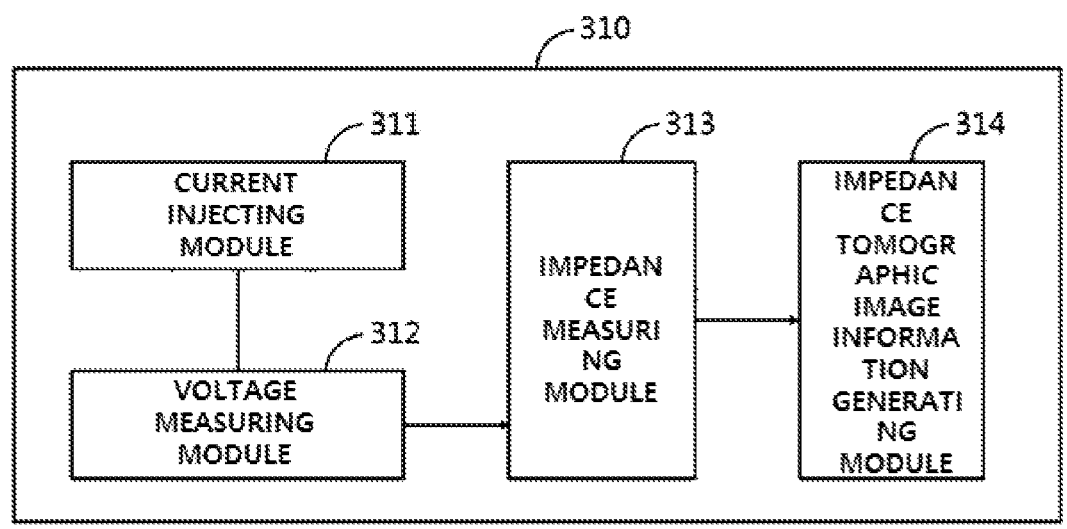
FIG. 4 is a block diagram illustrating a configuration of an image outputter of a sleep monitoring device according to an example embodiment.

FIG. 4 is a block diagram illustrating a configuration of an image outputter of a sleep monitoring device according to an example embodiment.

Referring to FIG. 4, the image outputter 310 may include a current injecting module 311 and a voltage measuring module 312.

The current injecting module 311 may inject currents having a plurality of frequency ranges through at least one EIT electrode pair selected from the plurality of EIT electrodes attached to the measurement target part.

In further detail, the current injecting module 311 may inject currents including frequency ranges of tens of hertz (Hz) to a few megahertz (MHz) through an EIT electrode pair selected from a plurality of EIT electrodes formed to be attached to at least one of the upper airway and the chest of the user.

The voltage measuring module 312 may measure a voltage induced in response to the injected currents through an EIT electrode pair unselected from the plurality of EIT electrodes.

According to an example embodiment, the current injecting module 311 and the voltage measuring module 312 may inject the currents through the selected EIT electrode pair based on vertical and horizontal directions of the biological tissue and measure the induced voltage, to show electrical properties of the biological tissue of the measurement target part of the user from the controller 340 of the sleep apnea monitoring system.

In addition, the image outputter 310 may further include an impedance measuring module 313 and an impedance tomographic image information generating module 314.

The impedance measuring module 313 may measure the impedance data based on the voltage measured through the voltage measuring module 312, the voltage that changes depending on the sleeping state of the user.

The impedance measuring module 313 may measure the impedance data of the biological tissue of the measurement target part including the upper airway and the chest based on the voltage measured by the voltage measuring module 312 in relation to a shape of obstruction of the upper airway and the chest appearing when the user is in the sleeping state.

According to an example embodiment, the impedance measuring module 313 may measure impedance data of a vertical direction of the measurement target part and impedance data of a horizontal direction of the measurement target part based on induced voltages measured based on the vertical and horizontal directions of the measurement target part including the upper airway and the chest.

Also, the impedance measuring module 313 may perform inverse non-linear data processing using the measured impedance data, thereby estimating a distribution of impedance at the measurement target part of the user.

The impedance tomographic image information generating module 314 may generate the impedance tomographic image information by imaging the properties of the biological tissue based on the measured impedance data.

The impedance tomographic image information generating module 314 may obtain impedance tomographic image information of a predetermined region of the biological tissue of the measurement target part from impedance data with respect to a predetermined target part of the user through a plurality of EIT electrodes within a range of use measured by the EIT electrode unit.

For example, the impedance tomographic image information generating module 314 may generate the impedance tomographic image information from a change in the impedance data with respect to a change in the shape of the lungs in response to respiration of the user and an aspect of obstruction of the upper airway of the user.

Referring to FIG. 3 again, the biosignal analyzer 320 of the sleep monitoring device 300 may analyze the biosignal including at least one of a blood oxygen saturation, a sound, a position and an ECG of the measurement target part of the user sensed by the sensing unit.

The biosignal analyzer 320 may receive the sensed biosignal of the user from the sensing unit and analyze the biosignal based on a preset reference value.

For example, the biosignal analyzer 320 may receive a biosignal including a sound, sense the sound of at least one of breathing, snoring, crying and talking in sleep, and analyze at least one of a risk level, an average and an intensity of the biosignal with respect to the sound based on a preset reference value of sound.

Also, the biosignal analyzer 320 may receive a biosignal including a position, sense a position based on a movement of the user, and analyze at least one of a supine position, a lateral position, a sitting position, and a standing position.

Also, the biosignal analyzer 320 may receive a biosignal including at least one of a blood oxygen saturation and an ECG and analyze a risk level of the biosignal with respect to the blood oxygen saturation and the ECG based on a preset reference value.

The sleeping state detector 330 may detect the sleeping state of the user based on the output impedance tomographic image information and the analyzed biosignal.

The sleeping state detector 330 may detect a sleeping state of respiration or apnea of the user from ECG morphology by the output impedance tomographic image information and the analyzed biosignal.

For example, the sleeping state detector 330 may obtain a peak interval of an ECG biosignal based on a heart rate variability occurring at the chest, which is called respiratory sinus arrhythmia, and detect a respiration signal by applying interpolation to the interval. Thus, the sleeping state detector 330 may detect an apnea state from the respiration signal.

That is, the sleeping state detector 330 may detect the sleeping state of respiration or apnea of the user based on the impedance tomographic image information output with respect to the chest of the user and the ECG biosignal.

The sleeping state detector 330 may detect a sleeping state of obstructive sleep apnea or central sleep apnea based on the output impedance tomographic image information and the biosignal, in a case in which the sleeping state of apnea is detected.

For example, the sleeping state detector 330 may detect the sleeping state of obstructive sleep apnea that repeatedly causes frequent arousal and a decrease in a blood oxygen saturation due to a disorder in the air flow through the upper airway of the user or central sleep apnea in which apnea occurs for more than 10 seconds, based on the output impedance tomographic image information and the biosignal.

Also, the sleeping state detector 330 may detect a sleeping state of at least one of rapid eye movement (REM) sleep or non-REM sleep of the user based on the output impedance tomographic image information and the analyzed biosignal.

For example, the sleeping state detector 330 may detect the sleeping state of REM sleep or non-REM sleep based on a respiration rhythm or a change in respiratory rate when the user is sleeping based on the impedance tomographic image information output with respect to the upper airway or the chest of the user and the biosignal.

Also, the sleeping state detector 330 may detect a sleeping state of sleep or wake of the user based on the output impedance tomographic image information and a heart rate analyzed from an ECG when the ECG is measured as the biosignal.

For example, the sleeping state detector 330 may verify whether the user is in the sleeping state by analyzing the heart rate biosignal and detect the sleeping state of sleep or wake of the user based on the impedance tomographic image information with respect to the upper airway and the chest of the user to increase an accuracy further.

The sleeping state detector 330 may detect, according to an example embodiment, a sleeping state of a patient more accurately based on at least one of history data of the user and prescription and examination data related to the sleeping state that are stored and maintained in an external server of a clinic or a sleeping state management server and received from a communicator 360.

The controller 340 may control diagnosis information with respect to the detected sleeping state to be provided to the user.

For example, the controller 340 may control the diagnosis information with respect to the sleeping state including at least one of respiration, apnea, obstructive sleep apnea, central sleep apnea, sleep, wake, REM sleep and non-REM sleep to be provided to the user.

According to an example embodiment, the diagnosis information may be diagnosis information determined based on a manual corresponding to a preset sleeping state and diagnosis information with respect to a sleeping state received from the external server.

The controller 340 may control the image outputter 310 to measure the impedance data with respect to at least one of the upper airway and the chest of the user and control the biosignal analyzer 320 to measure the biosignal with respect to the measurement target part.

Also, the controller 340 may control at least one of the current injecting module 311, the voltage measuring module 312, the impedance measuring module 313 and the impedance tomographic image information generating module 314 to measure impedance data of vertical and horizontal directions with respect to at least one of the upper airway and the chest of the user.

Also, the controller 340 may control a user interface (UI) 350 to display the diagnosis information with respect to the detected sleeping state for the user and control the communicator 360 to transmit the diagnosis information with respect to the detected sleeping state to an external device.

The sleep monitoring device 300 may further include the UI 350 and the communicator 360.

The UI 350 may display at least one of the detected sleeping state, the diagnosis information with respect to the sleeping state and the output impedance tomographic image information for the user.

For example, the UI 350 may provide information related to the sleeping state to the user in real time by displaying at least one of the detected sleeping state, the diagnosis information and the impedance tomographic image information using at least one of a figure, a value, percent, a graph, an image and a drawing, and quantify an amount of respiration during sleep and display the quantified amount of respiration using at least one of an image, a signal and a figure.

The communicator 360 may transmit the diagnosis information with respect to the sleeping state and receive the diagnosis information with respect to the sleeping state and the information related to the sleeping state of the user from the external device.

For example, the communicator 360 may transmit at least one of the detected sleeping state, the diagnosis information and the impedance tomographic image information to a terminal owned by the user and, according to an example embodiment, transmit the same to at least one of the clinic and the sleeping state management server.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents.

Therefore, other implementations, other example embodiments and equivalents of the claims are within the scope of the following claims.

What is claimed is:

1. A sleep apnea monitoring system, comprising:
an electrical impedance tomography (EIT) electrode unit including a plurality of EIT electrodes to be attached to a surface of a chest of a user to measure impedance data on air distribution in lungs;
a sensing unit to be in contact with the measurement target part of the user to sense a biosignal; and
a sleep monitoring device configured to output impedance tomographic image information about properties of biological tissue of the chest based on the measured impedance data on air distribution in the lungs and monitor a sleeping state of the user based on respiratory volume obtained from the output impedance tomographic image information and the sensed biosignal,
wherein the sensing unit comprises:
at least one of a sound detecting sensor configured to sense a sound of at least one of breathing, snoring, crying and talking in sleep;
a blood oxygen saturation measuring sensor configured to measure a blood oxygen saturation signal in arterial blood of the measurement target part when the user is in the sleeping state;
an electrocardiogram (ECG) measuring sensor configured to measure an ECG of the measurement target part when the user is in the sleeping state; and
a position measuring sensor configured to detect a change in a sleeping position of the user in response to the user lying while sleeping, the user sitting while being awake or the user standing while being awake.

2. The sleep apnea monitoring system of claim 1, wherein the sleep monitoring device configured to output the impedance tomographic image information by imaging the properties of the biological tissue of the chest based on the measured impedance data, and
wherein the sleep monitoring device comprises:
a biosignal analyzer configured to analyze the biosignal including at least one of the blood oxygen saturation, the sound, the position, and the electrocardiogram (ECG) of the measurement target part of the user sensed by the sensing unit;
a sleeping state detector configured to detect the sleeping state of the user based on the output impedance tomographic image information and the analyzed biosignal; and
a controller configured to control diagnosis information with respect to the detected sleeping state to be provided to the user.

3. The sleep apnea monitoring system of claim 2, wherein the sleep monitoring device configured to inject currents having a plurality of frequency ranges through at least one EIT electrode pair selected from the plurality of EIT electrodes attached to the chest, and
measure an induced voltage in response to the injected currents through an EIT electrode pair unselected from the plurality of EIT electrodes.

4. The sleep apnea monitoring system of claim 3, wherein the sleep monitoring device configured to measure impedance data based on the measured voltage that changes depending on the sleeping state of the user, and
generate the impedance tomographic image information by imaging the properties of the biological tissue based on the measured impedance data.

5. The sleep apnea monitoring system of claim 2, wherein the sleeping state detector is configured to detect a sleeping state of respiration or apnea of the user from ECG morphology by the output impedance tomographic image information and the analyzed biosignal.

6. The sleep apnea monitoring system of claim 5, wherein the sleeping state detector is configured to detect a sleeping state of obstructive sleep apnea or central sleep apnea based on the output impedance tomographic image information and the analyzed biosignal.

7. The sleep apnea monitoring system of claim 2, wherein the sleeping state detector is configured to detect a sleeping state of rapid eye movement (REM) sleep or non-REM sleep of the user based on the output impedance tomographic image information and the analyzed biosignal.

8. The sleep apnea monitoring system of claim 2, wherein the sleeping state detector is configured to detect a sleeping state of sleep or wake of the user based on the output impedance tomographic image information and a heart rate analyzed from an ECG, when the ECG is measured as the biosignal.

9. The sleep apnea monitoring system of claim 2, wherein the sleep monitoring device further comprises:
a user interface (UI) configured to display at least one of the detected sleeping state, the diagnosis information with respect to the sleeping state, and the output impedance tomographic image information for the user; and
a communicator configured to transmit the diagnosis information with respect to the sleeping state.

10. The sleep apnea monitoring system of claim 1, wherein the plurality of EIT electrodes are arranged on one surface of a base plate formed of a flexible material and attached to the surface of the chest.

11. A sleep apnea monitoring system configured to output impedance tomographic image information by imaging properties of biological tissue of a chest of a user based on impedance data on air distribution in lungs measured in a plurality of electrical impedance tomography (EIT) electrodes to be attached to a surface of the chest of the user,
the system comprising:
a sensing unit to be in contact with a measurement target part of a user to sense a biosignal;
a biosignal analyzer configured to analyze a biosignal including at least one of a blood oxygen saturation, a sound, a position, and an electrocardiogram (ECG) of the measurement target part of the user sensed by the sensing unit being in contact with the measurement target part of the user;
a sleeping state detector configured to detect a sleeping state of the user based on respiratory volume obtained from the output impedance tomographic image information and the analyzed biosignal; and
a controller configured to control diagnosis information with respect to the detected sleeping state of the user to be provided to the user,
wherein the sensing unit comprises:
at least one of a sound detecting sensor configured to sense the sound of at least one of breathing, snoring, crying and talking in sleep;
a blood oxygen saturation measuring sensor configured to measure the blood oxygen saturation in arterial blood of the measurement target part when the user is in the sleeping state;
an ECG measuring sensor configured to measure the ECG of the measurement target part when the user is in the sleeping state; and a position measuring sensor configured to detect a change in the position of the user in response to the user lying while sleeping, the user sitting while being awake or the user standing while being awake.

* * * * *